(12) United States Patent
Bailey et al.

(10) Patent No.: US 11,960,665 B2
(45) Date of Patent: Apr. 16, 2024

(54) SYSTEMS AND METHODS OF STEERABLE ELONGATE DEVICE

(71) Applicant: Intuitive Surgical Operations, Inc., Sunnyvale, CA (US)

(72) Inventors: David W. Bailey, Portola Valley, CA (US); Federico Barbagli, San Francisco, CA (US); Reuben D. Brewer, Millbrae, CA (US); Christopher R Carlson, Belmont, CA (US); Vincent Duindam, San Francisco, CA (US); Tania K. Morimoto, Redwood City, CA (US); Michael D. Paris, San Francisco, CA (US); Oliver J. Wagner, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 424 days.

(21) Appl. No.: 17/407,634

(22) Filed: Aug. 20, 2021

(65) Prior Publication Data

US 2021/0378763 A1 Dec. 9, 2021

Related U.S. Application Data

(63) Continuation of application No. 16/314,317, filed as application No. PCT/US2017/039808 on Jun. 28, 2017, now Pat. No. 11,116,586.

(Continued)

(51) Int. Cl.
*A61B 46/10* (2016.01)
*A61B 1/00* (2006.01)
(Continued)

(52) U.S. Cl.
CPC ...... *G06F 3/03547* (2013.01); *A61B 1/00042* (2022.02); *A61B 34/25* (2016.02);
(Continued)

(58) Field of Classification Search
CPC .................................. A61B 46/00; A61B 46/10
(Continued)

(56) References Cited

U.S. PATENT DOCUMENTS

| 4,919,113 A | | 4/1990 | Sakamoto et al. |
| 5,174,306 A | * | 12/1992 | Marshall ............... A61F 15/001 |
| | | | 206/439 |

(Continued)

FOREIGN PATENT DOCUMENTS

| CN | 101495023 A | 7/2009 |
| CN | 101918073 A | 12/2010 |

(Continued)

OTHER PUBLICATIONS

International Preliminary Report on Patentability for Application No. PCT/US2017/039808, dated Jan. 10, 2019, 17 pages (ISRG09200/PCT).

(Continued)

*Primary Examiner* — Jacob K Ackun
(74) *Attorney, Agent, or Firm* — Haynes & Boone, LLP.

(57) ABSTRACT

A drape for an input control console of an elongate device may comprise a main drape section configured to fit over the input control console via a main opening at one end of the main drape section. The drape may also comprise a plurality of pockets. Each of the plurality of pockets may include a pocket opening that is attached to a respective secondary opening in the main drape section. Each of the plurality of pockets may be configured to be anchored, at the pocket (Continued)

opening, to a side surface of a respective raised ring or bezel on the input control console using a respective tightening element.

20 Claims, 10 Drawing Sheets

Related U.S. Application Data

(60) Provisional application No. 62/357,272, filed on Jun. 30, 2016.

(51) Int. Cl.
*A61B 34/00* (2016.01)
*A61B 34/35* (2016.01)
*G06F 3/0354* (2013.01)
*A61B 34/20* (2016.01)
*A61B 34/30* (2016.01)
*A61B 90/00* (2016.01)
*A61M 25/01* (2006.01)

(52) U.S. Cl.
CPC .............. *A61B 34/35* (2016.02); *A61B 34/74* (2016.02); *A61B 46/10* (2016.02); *A61B 2034/2051* (2016.02); *A61B 2034/2061* (2016.02); *A61B 2034/301* (2016.02); *A61B 2090/3735* (2016.02); *A61M 25/0113* (2013.01)

(58) Field of Classification Search
USPC .................................. 128/852; 206/363, 440
See application file for complete search history.

(56) References Cited

U.S. PATENT DOCUMENTS

| | | | |
|---|---|---|---|
| 5,629,498 A * | 5/1997 | Pollock | A61B 90/98 177/244 |
| 6,380,732 B1 | 4/2002 | Gilboa | |
| 6,389,187 B1 | 5/2002 | Greenaway et al. | |
| 6,398,755 B1 | 6/2002 | Belef et al. | |
| 7,316,681 B2 | 1/2008 | Madhani et al. | |
| 7,772,541 B2 | 8/2010 | Froggatt et al. | |
| 8,900,131 B2 | 12/2014 | Chopra et al. | |
| 9,259,274 B2 | 2/2016 | Prisco | |
| 9,452,276 B2 | 9/2016 | Duindam et al. | |
| 11,116,586 B2 * | 9/2021 | Bailey | A61B 34/25 |
| 2002/0196335 A1 | 12/2002 | Ozawa | |
| 2003/0045778 A1 | 3/2003 | Ohline et al. | |
| 2003/0220566 A1 | 11/2003 | Mesaros et al. | |
| 2005/0020901 A1 | 1/2005 | Belson et al. | |
| 2006/0013523 A1 | 1/2006 | Childlers et al. | |
| 2009/0178685 A1 * | 7/2009 | Haines | A61B 46/00 128/853 |
| 2009/0255541 A1 | 10/2009 | Kaska | |
| 2010/0225209 A1 | 9/2010 | Goldberg et al. | |
| 2012/0071752 A1 | 3/2012 | Sewell et al. | |
| 2012/0080040 A1 | 4/2012 | Skora et al. | |
| 2015/0173836 A1 | 6/2015 | Pack et al. | |
| 2015/0231011 A1 | 8/2015 | Rogers | |
| 2015/0366618 A1 | 12/2015 | Higuchi et al. | |
| 2019/0076093 A1 | 3/2019 | Saroha et al. | |
| 2019/0323703 A1 * | 10/2019 | Baldwin | F21V 31/00 |
| 2020/0078104 A1 | 3/2020 | Bailey et al. | |
| 2023/0248463 A1 * | 8/2023 | Siebenhaar | A61B 46/23 128/852 |
| 2023/0363846 A1 * | 11/2023 | Czop | A61B 46/23 |

FOREIGN PATENT DOCUMENTS

| | | |
|---|---|---|
| CN | 103157170 A | 6/2013 |
| CN | 204169938 U | 2/2015 |
| JP | 2007130485 A | 5/2007 |
| KR | 20140037108 A | 3/2014 |
| WO | WO-2011143024 A1 | 11/2011 |
| WO | WO-2015089372 A1 | 6/2015 |
| WO | WO-2016025465 A1 | 2/2016 |
| WO | WO-2018005842 A1 | 1/2018 |

OTHER PUBLICATIONS

International Search Report and Written Opinion for Application No. PCT/US2017/039808, dated Nov. 13, 2017, 21 pages (ISRG09200/PCT).

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SYSTEMS AND METHODS OF STEERABLE ELONGATE DEVICE

RELATED APPLICATIONS

This patent application is a continuation of U.S. patent application Ser. No. 16/314,317 filed Dec. 28, 2018 which is a U.S. National Stage patent application of International Patent Application No. PCT/US2017/039808 filed on Jun. 28, 2017, the benefit of which is claimed, and claims priority to and the benefit of the filing date of U.S. Provisional Patent Application 62/357,272; entitled "SYSTEMS AND METHODS OF STEERABLE ELONGATE DEVICE," filed Jun. 30, 2016, each of which is incorporated by reference herein in its entirety.

FIELD

The present disclosure is directed to systems and methods for controlling a steerable elongate device.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. One such minimally invasive technique is to use a flexible and/or steerable elongate device, such as a catheter, that can be inserted into anatomic passageways and navigated toward a region of interest within the patient anatomy. Control of such an elongate device by medical personnel involves the management of several degrees of freedom including at least the management of insertion and retraction of the elongate device as well as steering of the device. In addition, different modes of operation may also be supported.

Accordingly, it would be advantageous to provide input controls that support intuitive control and management of flexible and/or steerable elongate devices, such as steerable catheters, that are suitable for use during minimally invasive medical techniques.

SUMMARY

The embodiments of the invention are best summarized by the claims that follow the description.

Consistent with some embodiments, an input control console for an elongate device includes a first input control having an infinite length of travel in a first direction, a second input control having an infinite length of travel in more than one direction, one or more transceivers for coupling the console to a control unit for the elongate device, and interface circuits for coupling the first input control and the second input control to the one or more transceivers. The first input control providing a first command suitable for controlling an insertion depth of the elongate device. The second input control providing second commands suitable for controlling steering of a distal end of the elongate device.

Consistent with some embodiments, a method of operating an elongate device includes a control unit of the elongate device receiving an insertion or retraction command from a first input control mounted on an input control console, controlling an insertion depth of the elongate device based on the insertion or retraction command, receiving a steering command from a second input control mounted on the input control console, and controlling steering of a distal end of the elongate device based on the steering command. The first input control has an infinite length of travel in a first direction. The second input control has an infinite length of travel in more than one direction.

Consistent with some embodiments, a surgical drape for an input control console of an elongate device includes a main drape section configured to fit over the input control console via a main opening at one end of the main drape section, and a plurality of pockets. Each of the plurality of pockets includes a pocket opening that is attached to a respective secondary opening in the main drape section. Each of the plurality of pockets is configured to be anchored, at the pocket opening, to a side surface of a respective raised ring or bezel on the input control console using a respective tightening element.

Consistent with some embodiments, a method of using a surgical drape with an input control console of an elongate device includes positioning a main drape section of the surgical drape over an input control console using a first opening at one end of the main drape section, aligning each of a plurality of pockets in the surgical drape over a respective raised ring or bezel on the input control console, anchoring a second opening in each of the plurality of pockets to the respective raised ring or bezel using a tightening element, and closing the first opening of the surgical drape using a closure element attached to the main drape section near the first opening. Each of the plurality of pockets is sized to enable user interaction with an underlying infinite length of travel control input located within a boundary of the respective raised ring or bezel to which it is anchored.

Consistent with some embodiments, a method of making a surgical drape with an input control console of an elongate device includes forming a plurality of pockets by folding respective first pieces of drape material in half and fusing together first sides of each respective first piece of drape material, attaching each of the plurality of pockets to a respective slit in a second piece of draping material by fusing respective second sides of a first opening in each of the plurality of pockets to third sides of the respective slit, folding the second piece of draping material and fusing together outer edges of the second piece of draping material to form a tube, fusing closed a first end of the tube, and attaching a closure element to a second opening in the surgical drape located at a second end of the tube opposite to the first end.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figure 1:
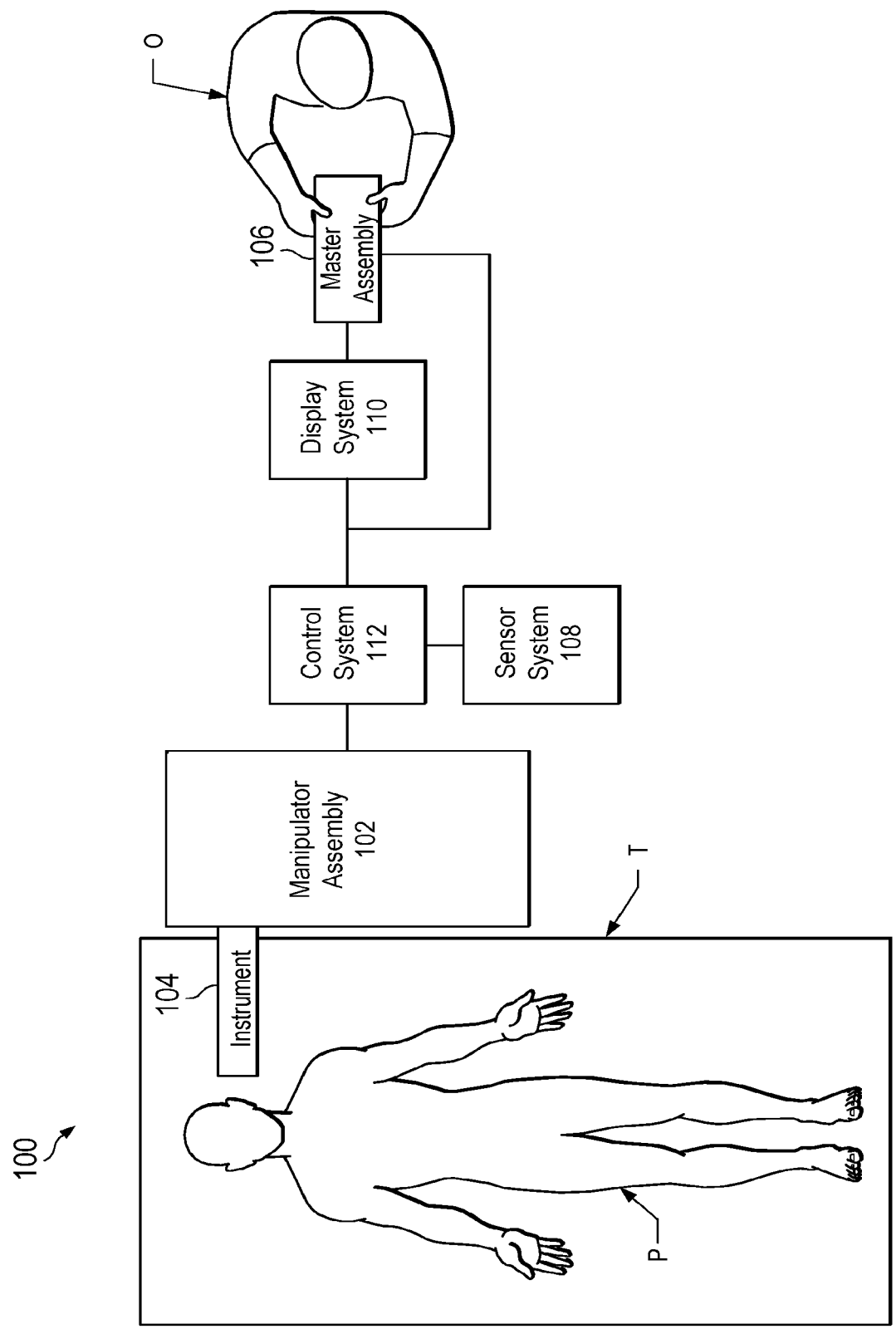
FIG. 1 is a simplified diagram of a teleoperated medical system according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

Any reference to surgical instruments and surgical methods is non-limiting as the instruments and methods described herein may be used for animals, human cadavers, animal cadavers, portions of human or animal anatomy, non-surgical diagnosis, industrial systems, and general robotic or teleoperational systems.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, medical system 100 generally includes a teleoperational manipulator assembly 102 for operating a medical instrument 104 in performing various procedures on a patient P. Teleoperational manipulator assembly 102 is mounted to or near an operating table T. A master assembly 106 allows an operator (e.g., a surgeon, a clinician, or a physician O as illustrated in FIG. 1) to view the interventional site and to control teleoperational manipulator assembly 102.

Master assembly 106 may be located at a physician's console which is usually located in the same room as operating table T, such as at the side of a surgical table on which patient P is located. However, it should be understood that physician O can be located in a different room or a completely different building from patient P. Master assembly 106 generally includes one or more control devices for controlling teleoperational manipulator assembly 102. The control devices may include any number of a variety of input devices, such as joysticks, trackballs, data gloves, trigger-guns, hand-operated controllers, voice recognition devices, body motion or presence sensors, and/or the like. To provide physician O a strong sense of directly controlling instruments 104 the control devices may be provided with the same degrees of freedom as the associated medical instrument 104. In this manner, the control devices provide physician O with telepresence or the perception that the control devices are integral with medical instruments 104.

In some embodiments, the control devices may have more or fewer degrees of freedom than the associated medical instrument 104 and still provide physician O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Teleoperational manipulator assembly 102 supports medical instrument 104 and may include a kinematic structure of one or more non-servo controlled links (e.g., one or more links that may be manually positioned and locked in place, generally referred to as a set-up structure) and a teleoperational manipulator. Teleoperational manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of teleoperational manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by sub-systems of sensor system 108. Display system 110 and master assembly 106 may be oriented so physician O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator or physician O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. In some examples, the endoscope may include one or more mechanisms for cleaning one or more lenses of the endoscope when the one or more lenses become partially and/or fully obscured by fluids and/or other materials encountered by the endoscope. In some examples, the one or more cleaning mechanisms may optionally include an air and/or other gas delivery system that is usable to emit a puff of air and/or other gasses to blow the one or more lenses clean. Examples of the one or more cleaning mechanisms are discussed in more detail in International Publication No. WO/2016/025465 (filed Aug. 11, 2016) (disclosing "Systems and Methods for Cleaning an Endoscopic Instrument"), which is incorporated by reference herein in its entirety. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of physician O. In this manner physician O can manipulate medical instrument 104 and the hand control as if viewing the workspace in substantially true presence. By true presence, it is meant that the presentation of an image is a true perspective image simulating the viewpoint of a physician that is physically manipulating medical instrument 104.

In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the physician O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist physician O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the physician O with a virtual image of medical instrument 104 within the surgical site from an external viewpoint. An image of a portion of medical instrument 104 or other graphical or alphanumeric indicators may be superimposed on the virtual image to assist physician O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to teleoperational manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of teleoperational manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, teleoperational manipulator assembly 102. In some embodiments, the one or more actuators and teleoperational manipulator assembly 102 are provided as part of a teleoperational cart positioned adjacent to patient P and operating table T.

Control system 112 may optionally further include a virtual visualization system to provide navigation assistance to physician O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system. Teleoperated medical system 100 may further include optional operations and support systems (not shown) such as illumination systems, steering control systems, irrigation systems, and/or suction systems. In some embodiments, teleoperated medical system 100 may include more than one teleoperational manipulator assembly and/or more than one master assembly. The exact number of teleoperational manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

Figure 2A:
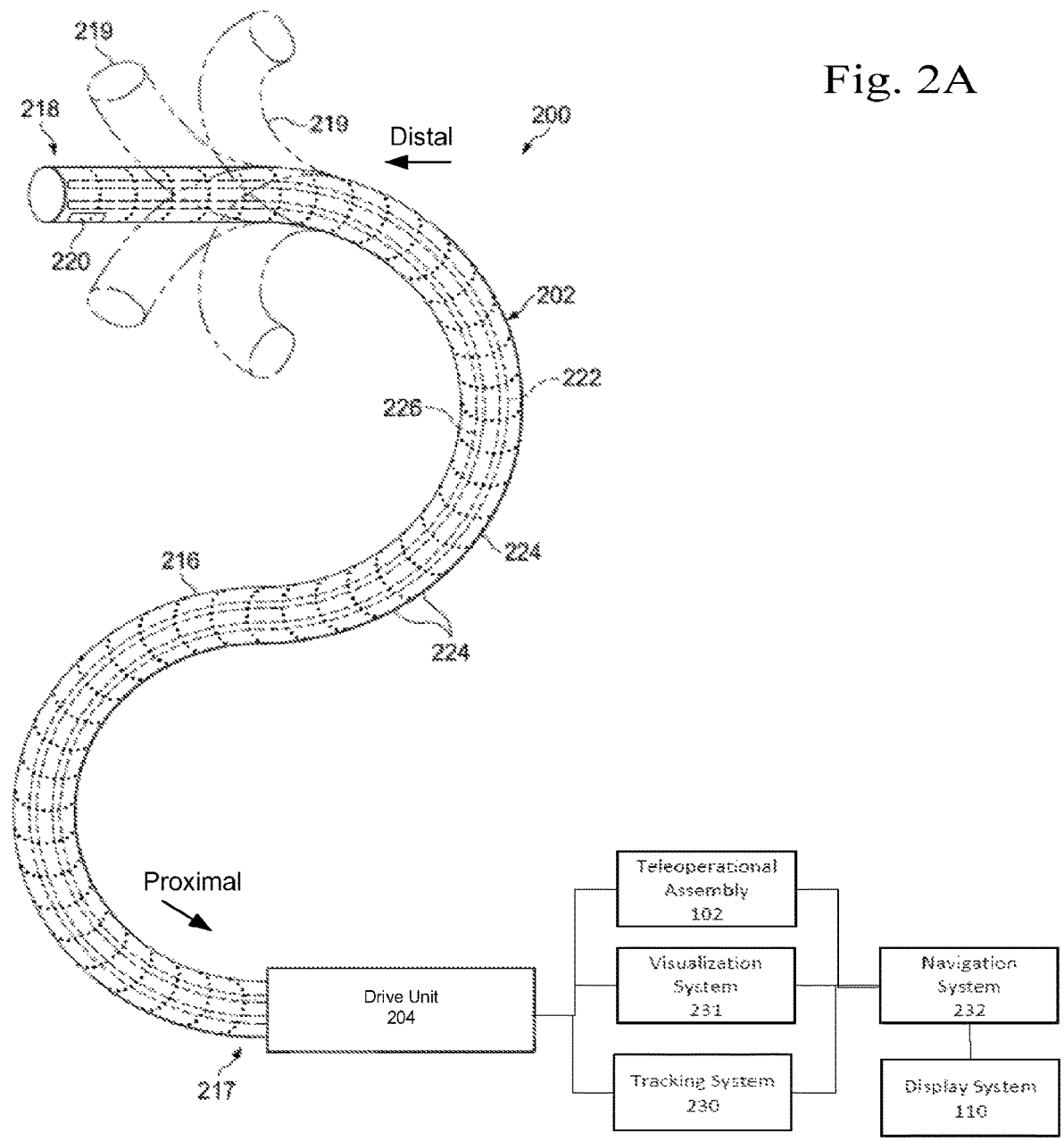
FIG. 2A is a simplified diagram of a medical instrument system according to some embodiments.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202, such as a flexible catheter, coupled to a drive unit 204. Elongate device 202 includes a flexible body 216 having proximal end 217 and distal end or tip portion 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 μm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may comprise, or be a component of an EM sensor system including one or more conductive coils that may be subjected to an externally generated electromagnetic field. Each coil of such an EM sensor system used to implement position sensor system 220 then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in embodiments of position sensor system 220 may be positioned along flexible body 216 and then used for shape sensing. In some examples, a history of data from one or more of these sensors taken during a procedure may be used to represent the shape of elongate device 202, particularly if an anatomic passageway is generally static.

Figure 2B:
FIG. 2B is a simplified diagram of a medical instrument with an extended medical tool according to some embodiments.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216. In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the physician or other operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, teleoperational manipulator assembly 102 of FIG. 1 may be replaced by direct operator control. In some examples, the direct operator control may include various handles and operator interfaces for hand-held operation of the instrument.

Figure 3A:
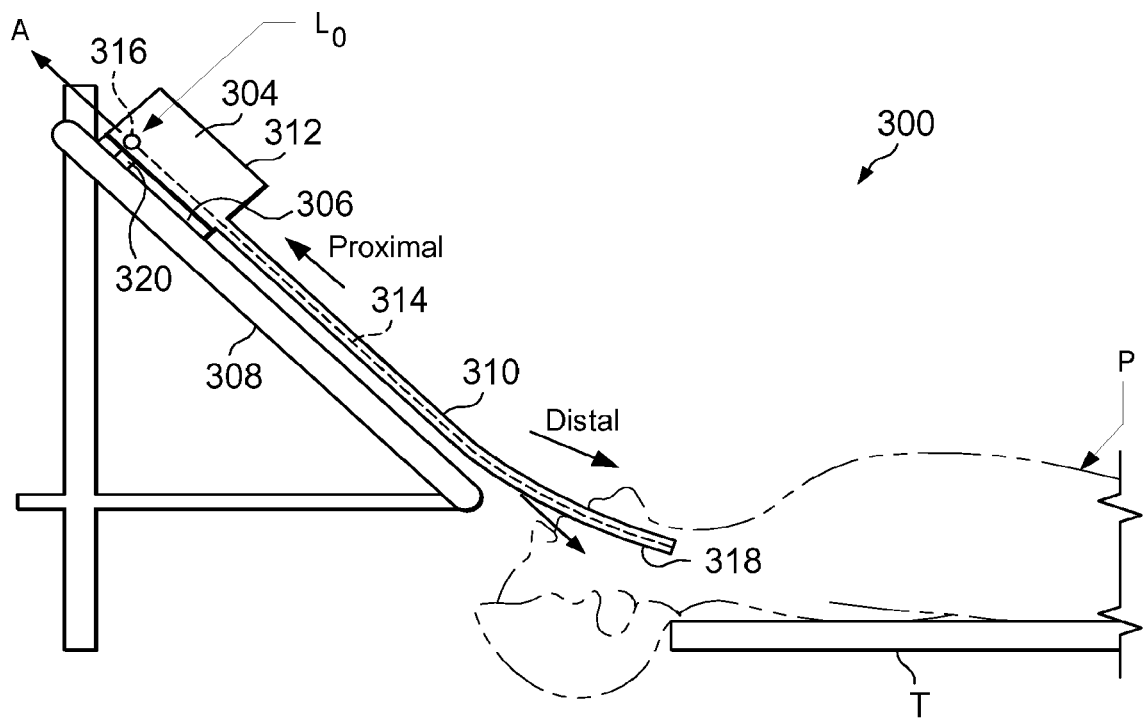
FIGS. 3A and 3B are simplified diagrams of side views of a patient coordinate space including a medical instrument mounted on an insertion assembly according to some embodiments.
Figure 3B:
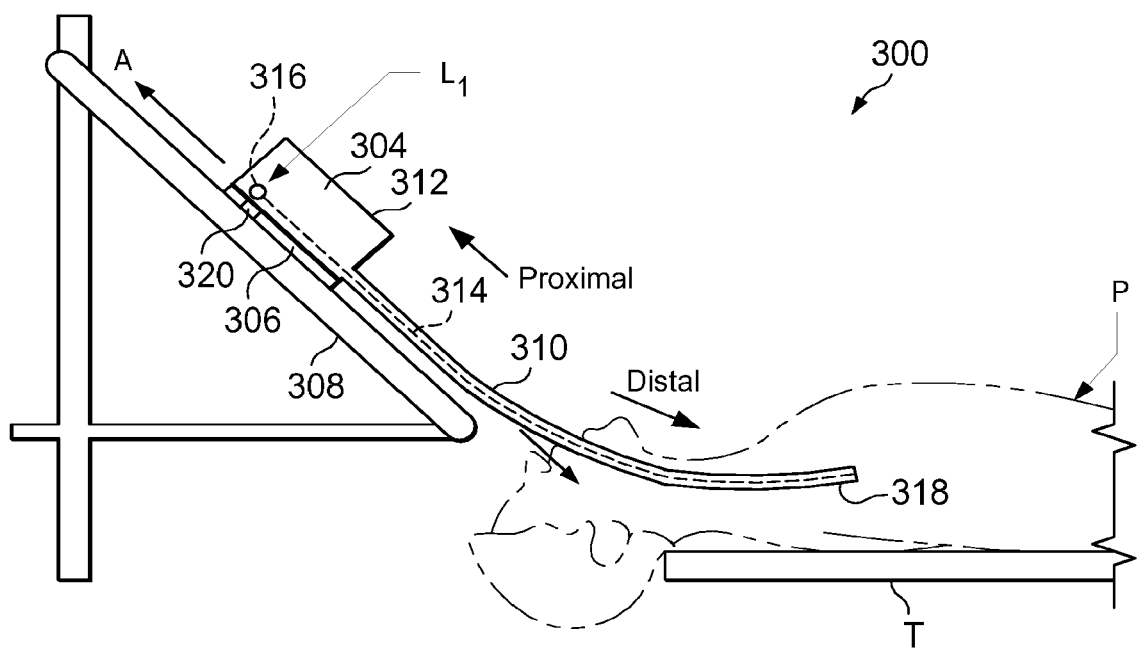

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P is positioned on platform 302. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 300, a point gathering instrument 304 is coupled to an instrument carriage 306. In some embodiments, point gathering instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a teleoperational manipulator assembly (e.g., teleoperational manipulator assembly 102) that couples to point gathering instrument 304 to control insertion motion (i.e., motion along the A axis) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308.

Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Point gathering instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position Lo on axis A. In this position along insertion stage 308 an A component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also in this position, position measuring device 320 may be set to a zero and/or the another reference value (e.g., 1=0). In FIG. 3B, instrument body 312 and instrument carriage 306 have advanced along the linear track of insertion stage 308 and distal end 318 of elongate device 310 has advanced into patient P. In this advanced position, the proximal point 316 is at a position L, on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position L. of proximal point 316 relative to position Lo. In some examples, position Lx may further be used as an indicator of the distance or insertion depth to which distal end 318 of elongate device 310 is inserted into the passageways of the anatomy of patient P.

Control of a flexible elongate device such as elongate device 202 having flexible body 216, elongate device 310, and/or a flexible catheter often involves the simultaneous control of multiple degrees of freedom. In some examples, to control insertion and/or retraction of the elongate device and correspondingly an insertion depth of the distal end of the elongate device, such as distal end 218 and/or 318, one or more actuators, such as the one or more actuators controlling the position of instrument carriage 306 along insertion stage 308, are used. Commands to the one or more actuators may be received from physician O using a single degree of freedom input control, such as a lever, joystick, and/or the like. In some examples, to control the steering of the distal end, the steering unit for the distal end, such as drive unit 204, is provided with both pitch and yaw instructions. The pitch and yaw instructions may be received from physician O using a two-degree of freedom input control, such as a joystick. Because control of the elongate device typically includes concurrently providing insertion and/or retraction instructions along with steering instructions, the input controls for insertion and/or retraction and steering are typically separate from each other.

For certain procedures, the use of levers and/or joysticks as the input controls for the elongate devices of FIGS. 2A, 3A, and/or 3B can be less than ideal. This is because levers and joysticks are input controls that have a finite length of travel, which are often disproportionately short relative to the length of insertion travel and/or the range of steering necessary to access certain anatomy. Thus, use of the levers and/or joysticks as positional input devices that provide a limited insertion depth, pitch setting, and/or yaw setting can be inadequate. Input controls with a finite length of travel are typically used as velocity input devices where either movement of the input control either specifies three velocity settings (reverse, idle, and forward) for switch-type input controls or variable velocity settings for proportional type input controls. However, velocity-based control of the insertion depth, pitch setting, and/or yaw setting is often unsatisfactory for high-precision manipulation of the elongate device as the control of the velocity of the distal end does not generally intuitively correspond with desires to make small high-precision changes in the insertion depth, pitch setting, and/or yaw setting, which is typically required for teleoperated minimally invasive medical procedures.

In contrast, input controls offering an infinite length of travel can offer better options as input controls for the elongate device when accessing certain anatomy. Input controls with an infinite length of travel correspond to input controls that allow continued movement of the inputs controls in a particular direction where no stop, such as a mechanical stop, restricts further movement. One example of a one degree of freedom input control with an infinite length of travel is a scroll wheel, which may be spun unendingly in either direction. One example of a multiple-degree of freedom input control with an infinite length of travel is a track ball, which may be spun unendingly about any number of axes, which in practice may be decomposed into combinations of a left and right rotation, a forward and back rotation, and a spin in place rotation. Other examples, of input controls that support an apparent infinite length of travel are input controls that support directional swipes without movement of the input control. Examples of directional swipe input controls are touch pads, touch screens, and/or the like.

Accordingly, it would be advantageous to develop input control units for elongate devices to provide input controls having infinite length of travel along with additional input controls to support the various modes of operation for elongate device.

Figure 4A:
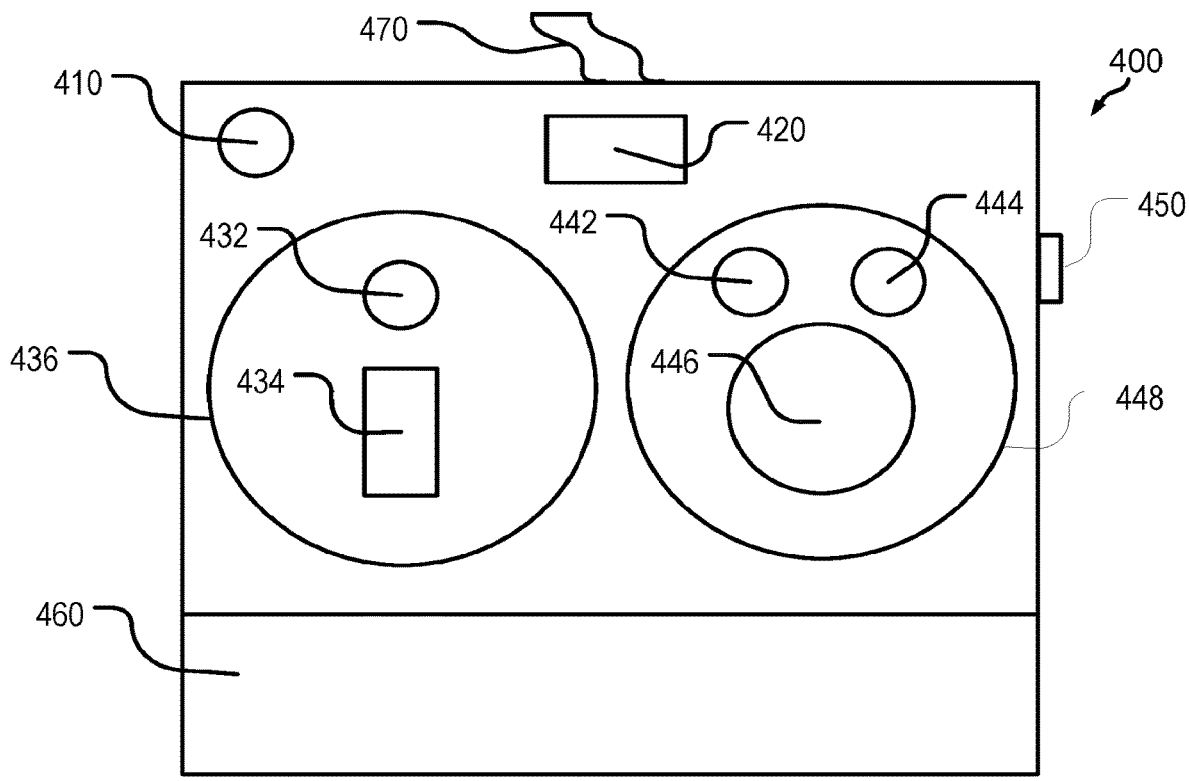
FIGS. 4A and 4B are simplified diagrams of top and side views, respectively, of an input control console for an elongate device according to some embodiments.
Figure 4B:
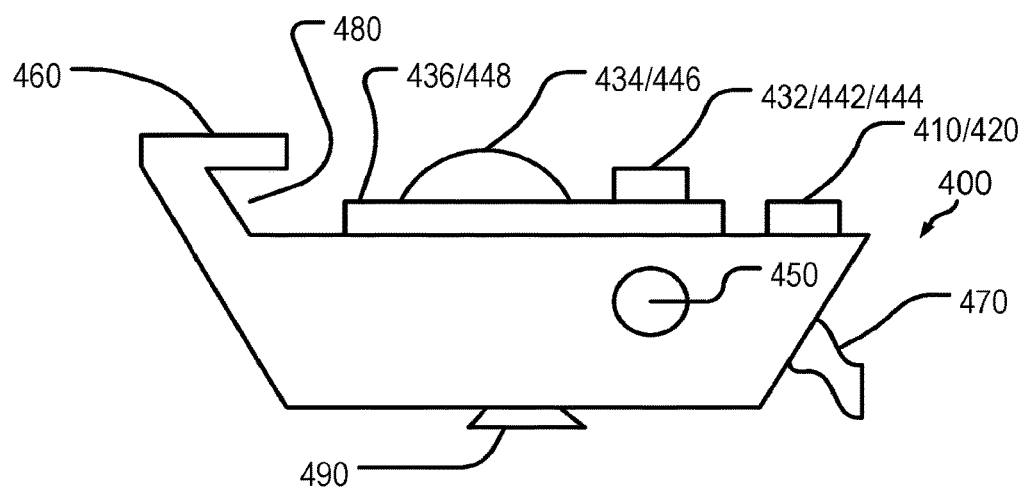

FIGS. 4A and 4B are simplified diagrams of top and side views, respectively, of an input control console 400 for an elongate device according to some embodiments. Although FIGS. 4A and 4B show configurations of various input controls for the elongate device, the exact placement, orientation, relative-positioning, and/or the like of the various input controls are exemplary only and it is understood that other configurations of input controls, different numbers of input controls, and/or the like are possible. In some embodiments, input control console 400 is suitable for use as a patient-side input control unit for the elongate device and may, for example, be mounted in proximity to insertion stage 308.

Although not shown in FIGS. 4A and 4B, input control console 400 may optionally include one or more circuit boards, logic boards, and/or the like that are usable to provide power, signal conditioning, interfacing, and/or other circuitry for input control console 400. In some examples, the one or more circuit boards, logic boards, and/or the like are useable to interface input control console 400 and its various input controls to a control unit for the elongate device. In some examples, the control unit of the elongate device corresponds to the control device of master assembly 106, control system 112, and/or the like. In some examples, the one or more circuit boards, logic boards, and/or the like may include memory and one or more one or more processors, multi-core processors, field programmable gate arrays (FPGAs), application specific integrated circuits (ASICs), and/or the like. In some examples, the memory may include one or more types of machine readable media. Some common forms of machine readable media may include floppy disk, flexible disk, hard disk, magnetic tape, any other magnetic medium, CD-ROM, any other optical medium, RAM, PROM, EPROM, FLASH-EPROM, any other memory chip or cartridge, and/or any other medium from which a processor or computer is adapted to read.

Input control console 400 includes an emergency stop button 410. In some examples, emergency stop button 410 may be wired as a normally closed switch that is directly coupled to the control unit for the elongate device and/or the actuators used to drive the elongate device so that the operator of the elongate device, such as physician O, may quickly interrupt control of the elongate device and cause the elongate device to enter a fail-safe state. In some examples, other configurations for emergency stop button 410 are possible including using a two-pole switch with a normally closed pole and a normally open pole. When any combination of positions for the poles are different than normally closed/normally open (e g, open/closed, closed/closed, and open/open) are detected, an emergency stop occurs. In some examples, emergency stop button 410 may optionally include one or more characteristics common to emergency stop buttons including a red coloration, a mushroom head, and/or the like. In some examples, emergency stop button 410 may optionally include suitable labeling, icons, and/or the like. In some examples, emergency stop button 410 may optionally be conditionally illuminated to indicate whether input control console 400 is properly connected to the elongate device, has been used to initiate an emergency stop, and/or the like.

Input control console 400 further includes a display selection switch 420. In some examples, display selection switch 420 may optionally be a multi-position slide switch, a toggle switch, a rocker switch, a rotary switch, and/or the like. In some examples, a toggle switch, a rocker switch, or similar may be used when two display modes are supported and a multi-position slide switch, a rotary switch, or similar may be used when two or more display modes are supported. In some examples, the operator uses display selection switch 420 to switch between display modes while operating the elongate device. In some examples, display selection switch 420 may optionally include labeling, color-coding, and/or the like indicating each display mode that may be selected using display selection switch 420. In some examples, a position of display selection switch 420 may optionally be indicated using one or more indicators, such as LEDs, illuminated icons, a display (e.g., a liquid crystal display), and/or the like. In some examples, display selection switch 420 is located so as to be operable by either hand of the operator.

In some examples, display selection switch 420 is usable to control the types of information displayed on display system 110. In some examples, the display modes may correspond to an alignment mode and a traversal mode. In some examples, the system is operating in the traversal mode when the distal end of the elongate device is a long distance from a desired target, such as a location chosen for a biopsy. While in the traversal mode, a traversal view is displayed to the operator. The traversal view may optionally include a live endoscopic view from an endoscope located at the distal end of the elongate device as well as a full or partial model of the anatomy of the patient, with or without a suggested navigation path for the elongate device superimposed. In some examples, the system is operating in the alignment mode when the distal end of the elongate device is near the target. While in the alignment mode, an alignment view is displayed to the operator. The alignment view may optionally include the live endoscopic view as well as targeting and/or alignment indicators to help the operator navigate the distal end to the target. In some examples, the targeting and/or alignment indicators may correspond to cross-hairs, a bull's eye, and/or the like. Further description of possible display modes and their features are provided in co-owned U.S. Patent Application Ser. No. 62/357,258 (filed Jun. 30, 2016) (disclosing "Graphical User Interface for Displaying Guidance Information in a Plurality of Modes During an Image-Guided Procedure"), which is incorporated by reference herein in its entirety. While the display selection switch 420 can be used to manually choose display of the traversal view or the alignment view, in alternative embodiments the traversal view and the alignment view could be displayed automatically based on known distance to the target based on sensor data, with display selection switch 420 providing an automatic view selection mode or alternatively being omitted.

Input control console 400, further includes an input control group including a camera cleaning button 432 and an insertion/retraction control 434. In some examples, camera cleaning button 432 and insertion/retraction control 434 are located so as to be operable by the same hand And, although camera cleaning button 432 and insertion/retraction control 434 are positioned for operation by the left hand of the operator, they could alternatively be located to the right side of input control console 400 for operation by the right hand of the operator.

In some examples, camera cleaning button 432 is a momentary push button, a momentary toggle switch, a momentary rocker switch, and/or the like for use in triggering cleaning of the imaging system, such as the endoscope located at the distal end of the elongate device. In some examples, camera cleaning button 432 may optionally include suitable labeling, icons, illumination, and/or the like. In some examples, activation of camera cleaning button 432 triggers the cleaning mechanisms of the endoscope to emit air and/or other gasses or liquids to clean one or more lenses of the endoscope. In some examples, the length of time camera cleaning button 432 is activated may control the amount of air and/or other gasses that are blown across the one or more lenses. In some example, camera cleaning button 432 may include two or more activation positions, which each activation position delivering a different amount of air and/or other gasses blown across the one or more lenses and/or liquids applied to the one or more lenses.

In some examples, insertion/retraction control 434 is a single degree of freedom infinite length of travel input control providing infinite length of travel along a first axis, such as a sealed or unsealed scroll wheel, usable by the operator to control the insertion depth of the distal end of the elongate device. In some examples, scrolling of the scroll wheel forward away from the operator increases the insertion depth (insertion) of the distal end and scrolling of the scroll wheel backward toward the operator decreased the insertion depth (retraction) of the distal end. In some examples, insertion/retraction control 434 is usable by the operator to move instrument carriage 306 in and out along insertion stage 308 in order to control the insertion depth of distal end 318. Because insertion/retraction control 434 is an infinite length of travel input control, operating insertion/retraction control 434 in a position-specifying mode allows the operator to exercise precise insertion depth control of the distal end of the elongate device over the full length of travel of the elongate device. In some examples, movement of insertion/retraction control 434 may be detected by the one or more circuit boards, logic boards, and/or the like of input control console 400 using one or more rollers, encoders, resolvers, optical sensors, hall effect sensors, and/or the like (not shown). In some examples, feedback applied to the one or more rollers, electromagnetic actuators, and/or the like may optionally be used to apply haptic feedback to insertion/retraction control 434. In some examples, a scale factor between an amount of movement of insertion/retraction control 434 and an amount of insertion and/or retraction movement by the elongate device is adjustable by the operator and/or control software of the elongate device so that an insertion/retraction velocity of the elongate device relative to an angular velocity of the scroll wheel may be adjusted to allow both fast insertion and retraction when advantageous and slower more precise insertion and retraction when greater control precision is desired.

In some embodiments, camera cleaning button 432 and insertion/retraction control 434 are optionally located within an optional raised ring 436 that extends above a top surface of input control console 400 and surrounds camera cleaning button 432 and insertion/retraction control 434. And although raised ring 436 is shown having a substantially circular shape, other shapes are possible including ovals, non-circular ellipses, squares, rectangles, polygons, partial versions of these shapes and/or the like. As shown, raised ring 436 provides a side surface around its circumference that is substantially perpendicular to the top surface of input control console 400. In some examples, the side surface is sufficiently high to provide a surface to which an opening in a pocket of a surgical and/or sterile drape may be anchored using an elastic member, a drawstring, and/or the like so that the opening in the pocket does not move relative to raised ring 436. In some embodiments, the side surface of raised ring 436 may be indented (not shown) to allow the elastic member, the drawstring, and/or the like to more securely anchor the opening in the pocket to raised ring 436. Use of a surgical and/or sterile drape with raised ring 436 is described in further detail below. In alternate embodiments, camera cleaning button 432 and insertion/retraction control 434 are optionally mounted on a top surface of a bezel that extends above the top surface of input control console 400 like a mesa or plateau instead of being located within raised ring 436.

Input control console 400, further includes an input control group including mode control inputs 442 and 444 and a steering control. In some examples, mode control inputs 442 and 444 and steering control 446 are located so as to be operable by the same hand. And, although mode control inputs 442 and 444 and steering control 446 are positioned for operation by the right hand of the operator, they could alternatively be located to the left side of input control console 400 for operation by the left hand of the operator.

In some examples, mode control inputs 442 and 444 are momentary push buttons, momentary toggle switches, momentary rocker switches, and/or the like for use selecting an operational mode of the elongate device. In some examples, mode control inputs 442 and 444 may each optionally include suitable labeling, icons, illumination, and/or the like. In some examples, the operational mode currently selected by mode control inputs 442 and 444 may be indicated by illuminating the mode control input 442 or 444 most recently activated. In some embodiments, separate mode control inputs 442 and 444 may optionally be replaced by an integrated input control such as a slide switch, a toggle switch, a rocker switch, a rotary switch, and/or the like. And although only two mode control inputs 442 and 444 are shown, additional mode control inputs are possible for elongate devices that support more than two operational modes.

In some examples, the possible operational modes for the elongate device correspond with a locked mode and a controlled mode. In some examples, the locked mode corresponds to a mode where insertion, retraction, and steering of the elongate device are disabled. In some examples, selection of locked mode using the mode control inputs 442 and 444 may result in the elongate device being held at a current insertion depth and with a current steering setting irrespective of operator manipulation of insertion/retraction control 434 and steering control 446. In some examples, the locked mode may be suitable for use when movement of the elongate device is disabled while an instrument inserted through the elongate device, such as medical tool 228, is operated at a target site. In some examples, controlled mode corresponds to a mode where active control of insertion, retraction, and/or steering of the elongate device is permitted using insertion/retraction control 434 and/or steering control 446.

In some examples, steering control 446 is a multiple degree of freedom infinite length of travel input control, such as a sealed or unsealed track ball providing infinite length of travel about any number of axes, which in practice may be decomposed into combinations of a left and right rotation, a forward and back rotation, and a spin in place rotation. Steering control 446 is usable by the operator to concurrently control both the pitch and yaw of the distal end of the elongate device. In some examples, components of the track ball rotation in the forward and back directions may be used to control a pitch of the distal end of the elongate device and components of the track ball rotation in the left and right directions may be used to control a yaw of the distal end of the elongate device. In some examples, other rotational components of the track ball may be used to control pitch and/or yaw with the operator being optionally able to control whether the direction of rotation is normal and/or inverted relative to the direction applied to the steering (e.g., rotate forward to pitch down and backward to pitch up versus backward to pitch down and forward to pitch up). In some examples, steering control 446 is usable by the operator to manipulate a desired bend angle of the distal ends of the elongate device. In some examples, the desired bend angle may then be used as a set point for the controller of the elongate devices that controls the distances and/or forces by which each of the cables extending between the proximal and distal ends of the elongate device are pushed and/or pulled to obtain the desired bend angle in the distal end of the elongate device. Because steering control 446 is an infinite length of travel input control, operating steering control 446 in a position-specifying mode allows the operator to exercise precise steering of the distal end of the elongate device in both pitch and yaw concurrently so as to achieve precise control over an orientation of the distal end. In some examples, movement of steering control 446 may be detected by the one or more circuit boards, logic boards, and/or the like of input control console 400 using one or more rollers, encoders, resolvers, optical sensors, hall effect sensors, and/or the like (not shown). In some examples, feedback applied to the one or more rollers, electromagnetic actuators, and/or the like may optionally be used to apply haptic feedback to steering control 446. In some examples, a scale factor between an amount of movement of steering control 446 and an amount of pitch and/or yaw imparted to the distal end of the elongate device of is adjustable by the operator and/or control software of the elongate device.

In some embodiments, mode control inputs 442 and 444 and steering control 446 are optionally located within a raised ring 448 that extends above a top surface of input control console 400 and surrounds mode control inputs 442 and 444 and steering control 446. And although raised ring 448 is shown having a substantially circular shape, other shapes are possible including ovals, non-circular ellipses, squares, rectangles, polygons, partial versions of these shapes and/or the like. As shown, raised ring 448 includes a side surface around its circumference that is substantially perpendicular to a top surface of input control console 400. In some examples, the side surface is sufficiently high to provide a surface to which an opening in a pocket of a surgical and/or sterile drape may be anchored using an elastic member, a drawstring, and/or the like so that the opening in the pocket does not move relative to raised ring 448. In some embodiments, the side wall of raised ring 448 may be indented (not shown) to allow the elastic member, the drawstring, and/or the like to more securely anchor the opening in the pocket to raised ring 448. Use of a surgical and/or sterile drape with raised ring 448 is described in further detail below. In alternate embodiments, mode control inputs 442 and 444 and steering control 446 are optionally mounted on a top surface of a bezel that extends above the top surface of input control console 400 like a mesa or plateau instead of being located within raised ring 448.

Input control console 400 further includes a passive control button 450. Although passive control button 450 is shown mounted on a side of input control console 400, location of passive control button 450 may optionally be elsewhere, such as part of mode control inputs 442 and 444. In some examples, passive control button 450 is a momentary push button, a momentary toggle switch, a momentary rocker switch, and/or the like for use in placing the elongate device in a passive control mode. In some examples, passive control button 450 may optionally include suitable labeling, icons, illumination, and/or the like. In some examples, activation of passive control button 450 results in reduction in the forces applied by the cables used to steer the distal end of the elongate device. As a result, the elongate device is placed in a highly flexible state that allows it to move and/or flex with the anatomic passages in which it is located. In some examples, activation of passive control button 450 may further disable use of insertion/retraction control 434 and/or steering control 446.

Input control console 400 further includes a raised wrist rest 460 usable to provide a resting point for the wrists of the operator and/or to provide good ergonomic positioning of the operator's hands over the other input controls. In some examples, wrist rest 460 is optionally padded. In some examples, a height of wrist rest 460 relative to the rest of input control console 400 is adjustable. As shown, wrist rest 460 further includes an undercut region 480 allowing for a gap between an underside of the wrist rest and the surface on which the input controls are mounted where portions of the pockets of the surgical and/or sterile drape may be positioned for freer movement without being pinned by the operator's wrists resting on wrist rest 460 as is described in further detail below.

Input control console 400 further includes one or more cables 470 to couple the input control console 400 to a power supply, the control unit for the elongate device, and/or the like. In some examples, the one or more cables 470 include a dedicated cable for connecting emergency stop button 410 to the fail-safe mechanisms of the elongate device. In some examples, the one or more cables 470 include one or more buses and/or communication cables to allow the one or more circuit boards, logic boards, and/or the like of input control console 400 and the control unit of the elongate device to exchange commands, status information, and/or the like. In some examples, the one or more buses and/or communications cables may be compatible with a communication standard, such as USB, RS-232, RS-485, SCSI, CAN, GPIB, and/or the like. In some examples, the one or more buses and/or communication cables are coupled to the one or more circuit boards, logic boards, and/or the like using one or more transceivers. In some examples, the one or more buses and/or communication cables are optional and may be replaced with one or more wireless transceivers supporting wireless communication using one or more of near-field communication (NFC), Bluetooth™, IrDA, HomeRF, IEEE 802.11, DECT, and Wireless Telemetry and/or the like. Although not shown, input control console 400 may further include one or more self-contained power sources (e.g., one or more batteries) and/or include one or more coils for receiving power inductively.

In some embodiments, input control console 400 may optionally include a mounting flange 490, threaded mount, and/or the like for securely mounting input control console 400 to a table, stand, mounting arm, and/or the like so that input control console 400 remains stable during operation of the input controls mounted thereon. In some examples, the mounting arm may be consistent with a Fisso Arm, available from Baitella AG, Zurich Switzerland, that it mountable to patient beds, surgical tables, and/or the like. In some embodiments, mounting flange 490 may include one or more interlocks (not shown) capable of detecting whether input control console 400 is properly mounted to the table, stand, mounting arm, and/or the like. When the one or more interlocks detect that input control console 400 is not properly mounted, they may trigger and emergency stop, place the system in lock mode, and/or the like. In some embodiments, one or more buttons, tabs, and/or the like (not shown) may also be used to prevent accidental dismounting of input control console by requiring actuation of the one or more buttons, tabs, and/or the like before dismounting may occur.

In some embodiments, use of the infinite length of travel input controls, such as the scroll wheel of insertion/retraction control 434 and/or the track ball of steering control 446, may not be ideal in all medical applications. In some examples, when a sealed scroll wheel and/or trackball are not used, the areas around the edges of the scroll wheel and/or the trackback where they intersect the surface of input control console introduce a gap that may be difficult to seal from bodily and other fluids that may come in contact with input control console 400. In addition, the various raised surfaces due to the input controls may be difficult to clean and/or make sterile to support a procedure when the operator alternates between contact with the patient and use of input control console 400.

In some embodiments, the sealing, cleaning, and sterilization problems may be addressed using a suitably designed surgical and/or sterile drape. Unfortunately, infinite length of travel input controls, such as the scroll wheel of insertion/retraction control 434 and/or the track ball of steering control 446, are not easily operable with conventional drapes. This is because finite length of travel input controls have a relatively short distance of travel and can typically be accommodated with a drape that is generally shaped to the control and offers limited flexibility to move with the finite length of travel input controls. For example, a keyboard or keypad drape only has to move as far as a key travels, a joystick drape can be shaped to the joystick and only has to move through the limited angular motion of the joystick. This approach, however, is not suitable for use with an infinite length of travel input control which may move a distance many times its size. For example, a full circle revolution of a scroll wheel or a track ball involves travel over three times the diameter of the scroll wheel or track ball. Accordingly, a drape that supports a wide range of travel is desirable for input control consoles with infinite length of travel input controls, such as those found on input control console 400.

In some embodiments, one solution to this problem is addressed by a drape that includes both a large surface area relative to the size of the infinite length of travel input control and an ability to position extended regions of that large surface area over each infinite length of travel input control. In some examples, the drape is also relatively thin and flexible so that the operator is able to easily conform the drape to a shape of each of the input controls (both infinite length of travel and otherwise) so as to limit interference with operation of each of the input controls. In some examples, a surface friction of the drape is also sufficiently high so that movement of the drape over each of the input controls by the operator, even with a relatively light tough, imparts sufficient force on the input controls to get the input controls to travel a same distance as the operator's fingers. In some examples, the drape is also largely transparent so as not to interfere with the ability of the operator to read labels, icons, illumination, and/or the like associated with the input controls.

Figure 5:
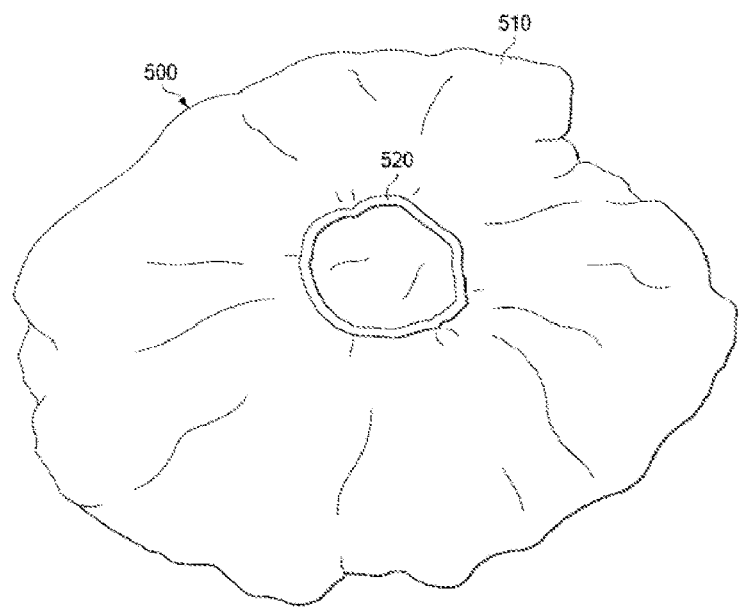
FIG. 5 is a simplified diagram of a drape for use with the input control console of FIGS. 4A and 4B according to some embodiments.

FIG. 5 is a simplified diagram of a drape 500 for use with input control console 400 according to some embodiments. As shown in FIG. 5, drape 500 includes a large sheet of drape material 510 with a much smaller elastic member 520 attached around the outer edges of drape material 510. Because the elastic member 520 is much smaller than the drape material 510, the edges of the drape material 510 are gathered together to create a bag or pocket shape with a relatively small opening. Elastic member 520 can then be stretched to an opening larger than input control console 400 and then placed over input control console 400 with elastic member positioned around the one or more cables 470 and the arm or other surface to which flange 490 is mounted.

The large size of drape material 510 allows it to fit loosely over the top of input control console 400 and more specifically the regions where insertion/retraction control 434 and steering control 446 are located. The loose fit of drape material 510 allows drape material 510 to move back and forth across insertion/retraction control 434 and/or steering control 446 without disturbing the ability of drape 500 to maintain an impermeable and/or sterile barrier between input control console 400 and the operator. In some examples, undercut region 480 below wrist rest 460 allows portions of drape material 510 to be situated between the operator's wrists on wrist rest 460 and insertion/retraction control 434 and/or steering control 446 so that the operator's wrists won't interfere significantly with that ability of the loose drape material 510 to move relative to insertion/retraction control 434 and/or steering control 446, thus allowing for extended range of travel for insertion/retraction control 434 and/or steering control 446 before excess drape material 510 is moved to one side of insertion/retraction control 434 and/or steering control 446 and has to be reset. In some examples, using a 1.0 to 2.0 mil clear polyethylene (PE) or low-density polyethylene (LDPE) as drape material 510 provides a good balance between transparency, durability, surface friction, and flexibility. In some examples, using rubber or other highly stretchable elastomer for elastic member 520 allows drape 500 to be stretched over input control console 400 while still providing closure around the one or more cables 470 and/or the mounting mechanism and allowing drape 500 to stay generally in place over input control console 400.

In some embodiments, the single pocket nature of drape 500 may interfere, somewhat, with independent operation of insertion/retraction control 434 and steering control 446. For example, a large amount of insertion or retraction movement in insertion/retraction control 434 may interfere with a large pitch movement of steering control 446, which rotates steering control 446 in a direction opposite to the rotation direction of insertion/retraction control 434. Accordingly, it would be advantageous to provide independent pockets over separate infinite length of travel input controls.

Figure 6:
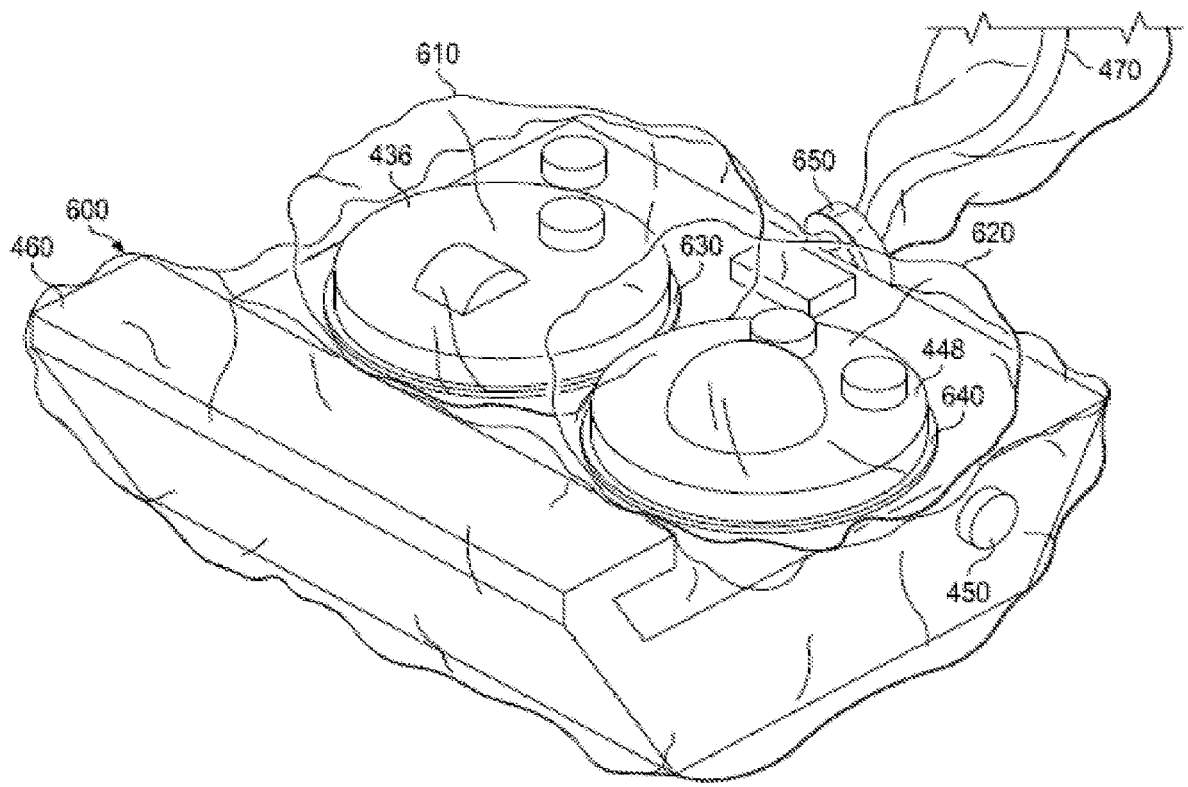
FIG. 6 is a simplified diagram of a drape with pockets for use with the input control console of FIGS. 4A and 4B according to some embodiments.

FIG. 6 is a simplified diagram of a drape 600 with pockets for use with input control console 400 according to some embodiments. As shown in FIG. 6, drape 600 includes separate pockets 610 and 620 configured to be positioned over insertion/retraction control 434 and steering control 446, respectively. The separate pockets 610 and 620 allow insertion/retraction control 434 and steering control 446 to be operated in opposite directions without drape 600 causing interference between them. The rest of drape 600 is largely tubular in shape to slip over input control console 400 with pockets 610 and 620 fused to separate openings in the tube that are spaced over raised rings 436 and 448, respectively. The openings in each of the pockets 610 and 620 are fit around their respective raised ring 436 or 448 and then secured in place using a respective elastic member 630 or 640. In some examples, the openings in each of the pockets 610 and 620 are slightly smaller than raised rings 436 and 448 so that the openings have to be slightly stretched to fit around raised rings 436 or 448 to improve overall retention of pockets 610 and 620 to raised rings 436 and 448, respectively. In some examples, elastic members 630 and 640 are integrated into drape 600 or alternatively applied separately after pockets 610 and 620 are positioned around raised rings 436 and 448. In some examples, elastic members 630 and/or 640 may alternatively be replaced with draw strings, tape strips, and/or the like. In some examples, the open end of the tube that forms drape 600 is secured in place over the one or more cables 470 and/or the mounting mechanism using a closure element 650, such as a draw string, tape strip, and/or the like to close the open end of the tube.

As with drape 500, in some examples, undercut region 480 below wrist rest 460 allows portions of pockets 610 and/or 620 to be situated between the operator's wrists on wrist rest 460 and insertion/retraction control 434 and/or steering control 446 so that the operator's wrists won't interfere significantly with that ability of pockets 610 and/or 620 to move relative to insertion/retraction control 434 and/or steering control 446.

In some embodiments, using a 1.0 to 2.0 mil clear PE or LDPE as the material in drape 600 provides a good balance between transparency, durability, surface friction, and flexibility. In some examples, the material in pockets 610 and/or 620 may be selected to be slightly thinner and more flexible than the material in the tube portion of drape 600. In some examples, pockets 610 and/or 620 may be formed from 1.0 to 1.5 mil LDPE and the tube part of drape 600 may be formed from 1.5 to 2.0 mil PE. In some examples, using rubber or other highly stretchable elastomer for elastic member 630 and/or 640 allows for easy, yet firm restraint of pockets 610 and 620 around raised rings 436 and 484, respectively.

Figure 7:
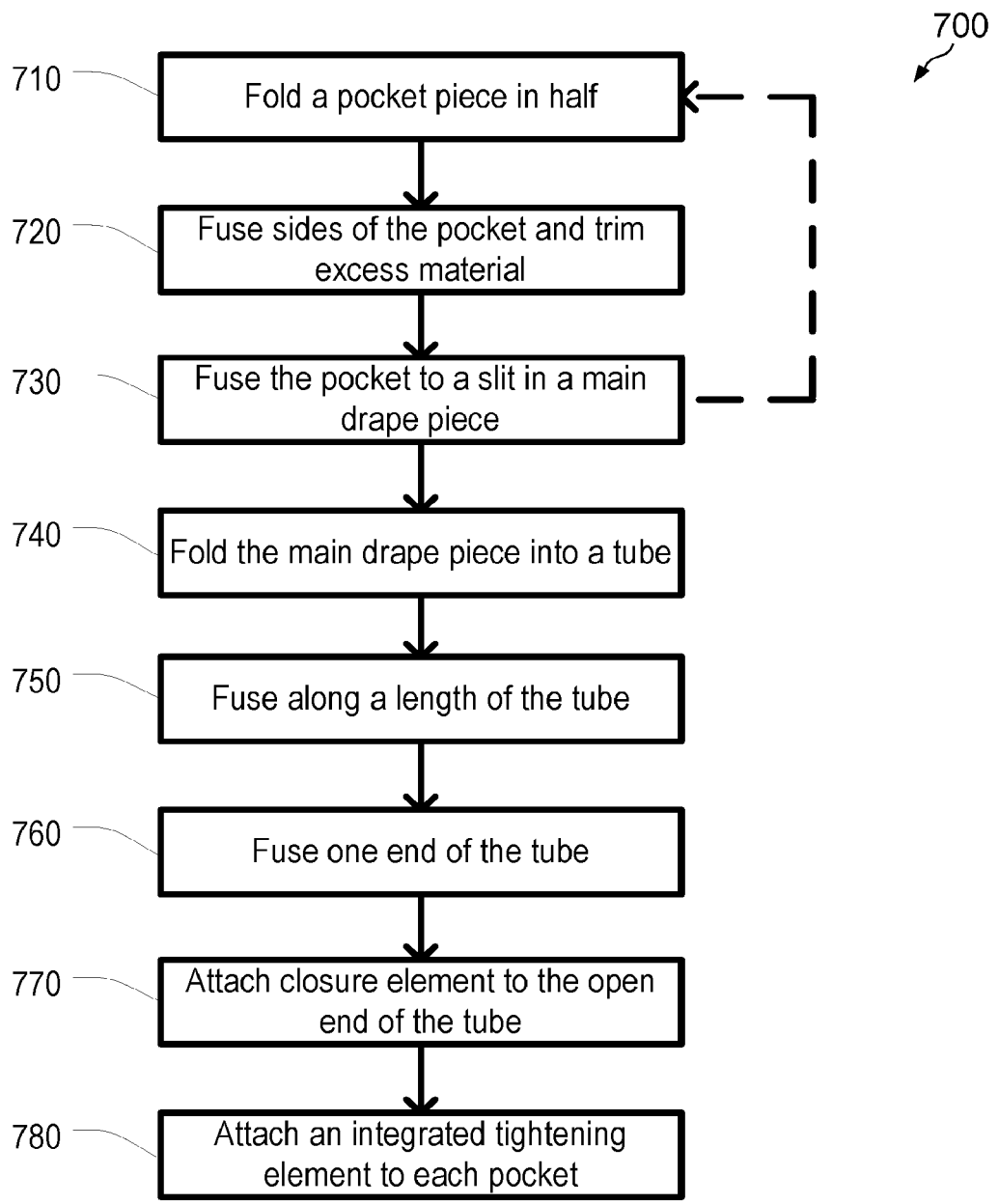
FIG. 7 is a simplified diagram of method of making the drape of FIG. 6 according to some embodiments.

FIG. 7 is a simplified diagram of method of making drape 600 according to some embodiments. The method 700 is illustrated in FIG. 7 as a set of operations or processes 710-780. Not all of the illustrated processes 710-780 may be performed in all embodiments of method 700. Additionally, one or more processes that are not expressly illustrated in FIG. 7 may be included before, after, in between, or as part of the processes 710-780. Processes 710-780 are described below in reference to FIGS. 8A-8F, which are simplified diagrams of a drape similar to drape 600 during various stages of assembly using processes 710-780 according to some embodiments. In some embodiments, process 780 is optional and may be omitted.

Figure 8A:
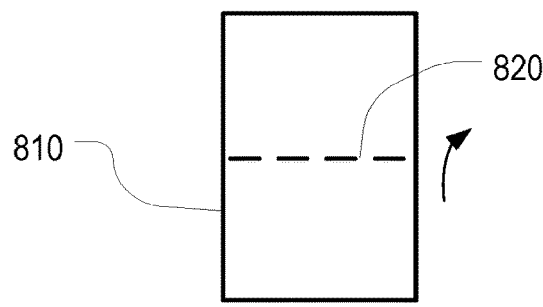
FIGS. 8A-8F are simplified diagrams of the drape of FIG. 6 during various stages of assembly according to some embodiments.

At a process 710, a pocket piece, such as pocket piece 810 in FIG. 8A, is folded in half along a center line 820. In some examples, pocket piece 810 is cut from a sheet of clear 1.0 to 1.5 mil LDPE.

Figure 8B:
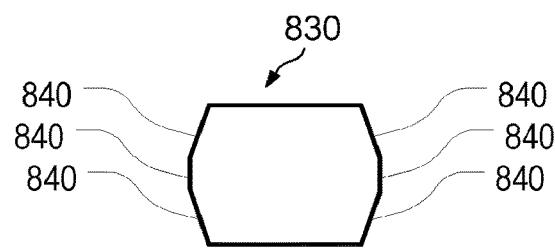
Figure 8C:
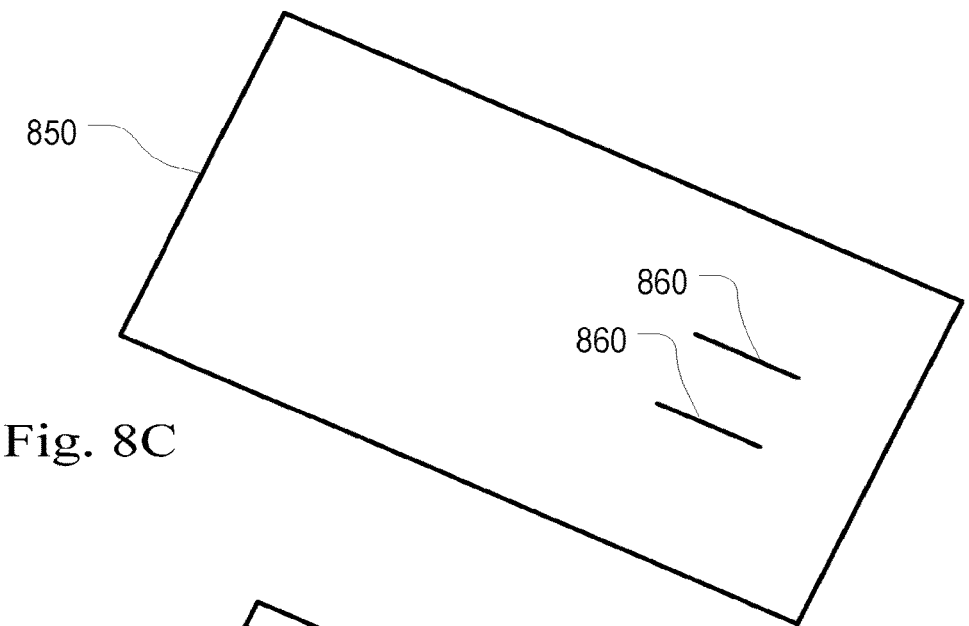

At a process 720, sides of the pocket are fused and excess material is trimmed. The side of pocket 830 opposite the fold is left unfused so that there is an opening in pocket 830, which will connect pocket 830 to drape 600. In some examples, the sides 840 may be fused together using heat, using a double-sided adhesive tape, and/or the like. As shown in FIG. 8B, pocket 730 has an approximately octagonal shape when laid flat. And although the shape shown in approximately octagonal, other shapes are possible including rectangles, other polygons, ovals, non-circular ellipses, circles, partial versions of these shapes and/or the like.

At a process 730, the pocket 830 is fused to a slit 860 in a main drape piece 850. In some examples, main drape piece 850 is formed from a large rectangular piece of draping material, such as clear 1.5 to 2.0 mil PE. Slits 860 are made in main drape piece 850 where each pocket 830 is to be attached. In some examples, a pocket 830 is fused to a slit 860 by inserting a separator material, such as a sheet of Teflon or other versions of polytetrafluoroethylene, between the two halves of pocket 830, pocket 830 is then inserted into slit 860 and the two halves are pocket 830 are heat fused to opposite sides of slit 860 and the separator material is removed. In some examples, pocket 830 may be alternatively attached to the two sides of slit 860 using double-sided tape or some other process.

Processes 710-730 are then repeated for each pocket 830 that are part of the drape. In the embodiments of drape 600, processes 710-730 would be performed twice, once for pocket 610 and once for pocket 620. After processes 710-730 are repeated the drape is consistent with the exemplary depiction in FIG. 8D.

Figure 8D:
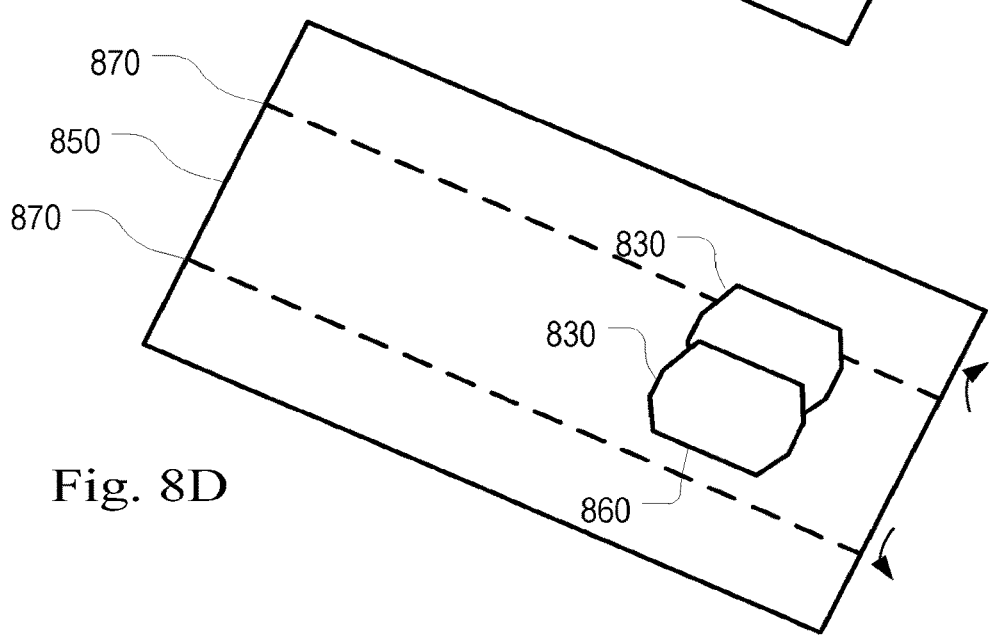
Figure 8E:
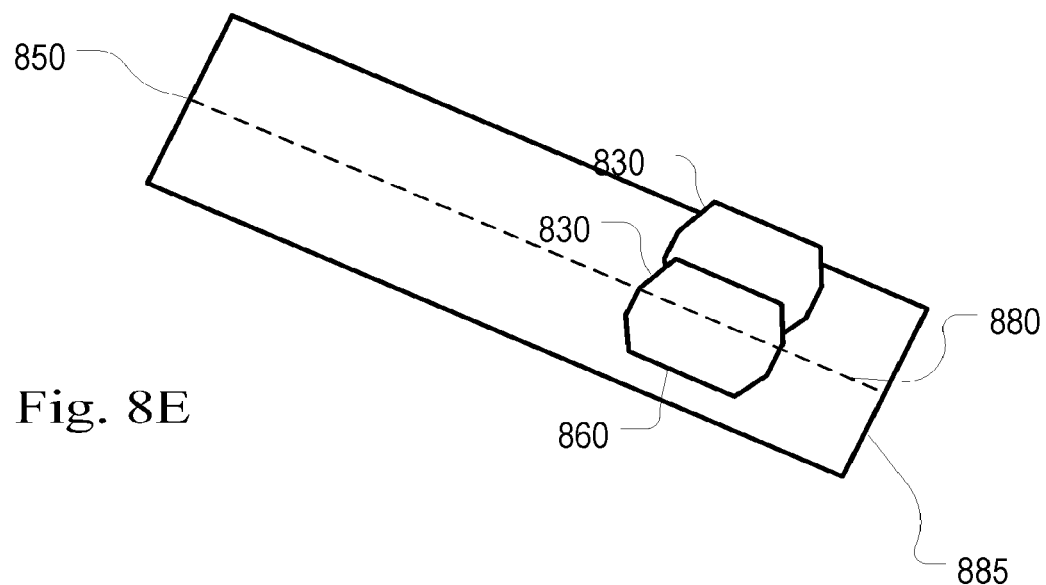

At a process 740, main drape piece is folded into a tube by folding along lines 880 as shown in FIG. 8D. Although two folds are shown in FIG. 8D, the tube could alternatively be shaped using a single fold that folded main drape piece 850 in half.

At a process 750, the tube is fused along its length. Where the two outer edges of main drape piece 850 meet after the folding of process 740, the two outer edges are fused together using heat, double-sided adhesive tape, and/or the like. The line of fusion during process 750 is depicted by dashed line 880 in FIG. 8F.

At a process 760, one end of the tube is fused. One end of the tube is fused shut, using heat, double-sided adhesive tape, and/or the like, to create a sock-like shape for the main section of the drape. The line of fusion is depicted by line 885 in FIG. 8E.

Figure 8F:
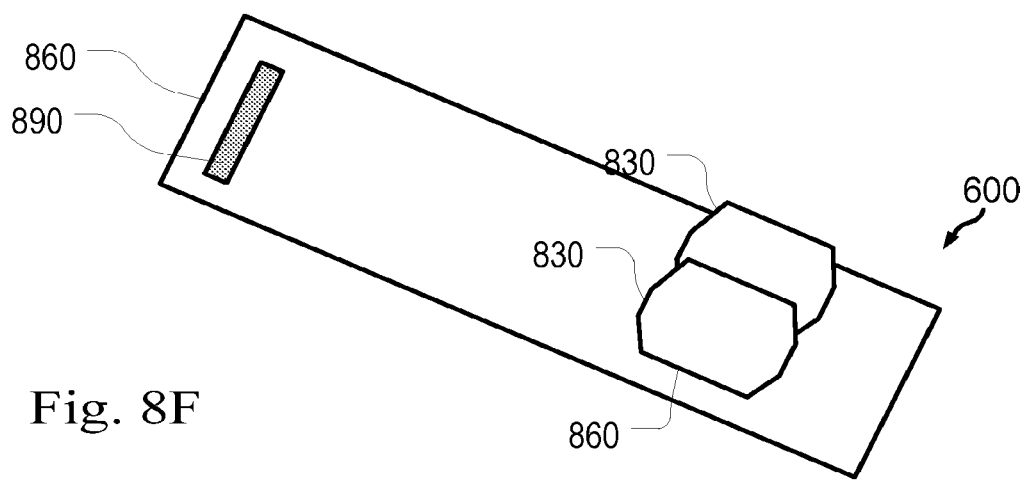

At a process 770, a closure element 890 is attached to the open end of the tube. In some examples, closure element 890 is consistent with closure element 650 and is formed using a draw string, a tape strip, and/or the like. Upon completion of process 770, drape 600 is formed as shown in FIG. 8F. In some embodiments, the open end of the tube may optionally be folded back to create a cuff that may make it easier to grab drape 600, open the open end to slip it over an input control console, and/or the like.

At an optional process 780, integrated tightening elements are attacked to each pocket 830. In some examples, each of the integrated tightening elements are used to secure a respective pocket 830 to a raised ring, such as raised rings 436 and/or 448. In some examples, each of the tightening elements may correspond to an elastic band, a drawstring, a tape strip, and/or the like. In some examples, the integrated tightening elements correspond to elastic members 630 and 640. In some examples, each of the tightening elements may be integrated by folding over the open end of each the pockets 830 to create a respective cuff before fusing each of the pockets 830 to a respective slit 860 during process 730. Each of the tightening elements may then be inserted into a respective one of the cuffs.

Figure 9:
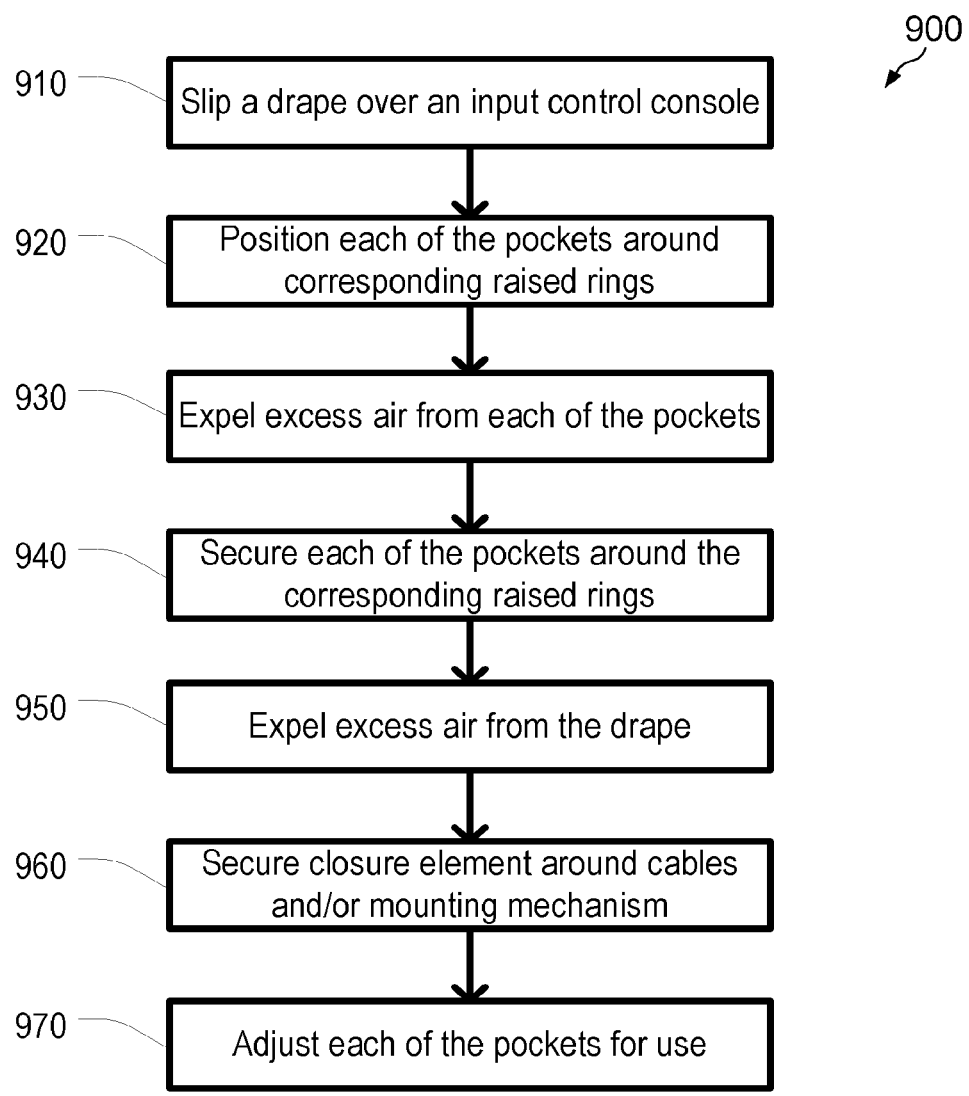
FIG. 9 is a simplified diagram of a method of using the using a drape with pockets according to some embodiments.

FIG. 9 is a simplified diagram of a method 900 of using the using a drape with pockets according to some embodiments. The method 900 is illustrated in FIG. 9 as a set of operations or processes 910-970. Not all of the illustrated processes 910-970 may be performed in all embodiments of method 900. Additionally, one or more processes that are not expressly illustrated in FIG. 9 may be included before, after, in between, or as part of the processes 910-970. In some embodiments, the drape of processes 910-970 is consistent with drape 600. In some embodiments, process 970 is optional and may be omitted.

At a process 910, a drape is slipped over an input control console. In some examples, the open end of the drape is spread open and slipped over the input control console. In the examples, of FIG. 6, process 910 includes opening drape 600 and slipping it over input control console 400 from the end with wrist rest 460 toward the end with the one or more cables 470.

At a process 920, each of the pockets in the drape, such as pockets 610, 620, and/or 830 are positioned around corresponding raised rings, such as raised rings 436 and/or 448. This allows each of the input controls mounted with each of the rings to have its own drape pocket to support a separate infinite travel input control.

At a process 930, excess air is expelled from each of the pockets. In order for the pockets to function effectively, there is a limited amount of air in the pocket so that it is easy to bring the surface of the pocket in contact with corresponding input controls. However, enough air should remain in the pocket so that the pocket may be moved freely relative to the input control to reposition and/or reset the pocket over the input controls without undue risk that such a movement will accidentally operate the input controls.

At a process 940, each of the pockets is secured around its corresponding raised ring. Using an elastic member or other tightening element, such as elastic member 630 and/or 640 and/or a tightening element integrated during process 780, the base of each pocket is securely attached to its corresponding raised ring so each pocket does not move relative to its corresponding raised ring.

At a process 950, excess air is expelled from the drape. Removal of the excess air allows the drape surface to be brought in proximity to each of the input controls not associated with a pocket, such as emergency stop button 410, display selection switch 420, and/or passive control button 450, so that those input controls may be operated without undue interference from the drape. Additionally, removal of the excess air will reduce interference by the main portion of the drape with any of the pockets.

At a process 960, a closure element, such as closure element 650 and/or 890, is secured around one or more cables, such as the one or more cables 470, and/or a mounting mechanism. Use of the closure element helps keep the drape in place over the input control console and also helps prevent the excess air expelled during process 950 from reentering the drape.

At an optional process 970, each of the pockets is adjusted for use. In some examples, one or more of the pockets may be centered over a corresponding infinite travel input control, such as insertion/retraction control 434 and/or steering control 446, to allow for travel in the control in a direction corresponding to each degree of freedom. In some examples, one or more of the pockets may be positioned largely to one side, such as for the pocket over insertion/retraction control 434 which is expected to have a large amount of insertion prior to a first retraction. In some examples, one or more of the pockets may be positioned in undercut region 480 to prevent the pockets from being trapped between wrist rest 460 and the operator's wrist.

Although drapes 500 and/or 600 simplify the use of input control console 400 in environments where a sterile field around a patient is used and/or to protect input control console 400 from liquids and/or other contaminants, use of drapes 500 and/or 600 does tend to interfere somewhat with the operator's ability to use input control console 400. Accordingly, it would be advantageous to have an input control console that supports infinite length of travel input controls, but which may optionally be used without a surgical and/or sterile drape. In some embodiments, sealed controls, such as sealed scroll wheels, sealed track balls, and/or the like may be used. In alternate embodiments, touch-sensitive input controls, such as touch pads, touch screens, and/or the like are able to provide infinite length of travel input controls while also making it easier to provide a sealed input control console that is easier to wipe down, clean, and/or make sterile.

Figure 10:
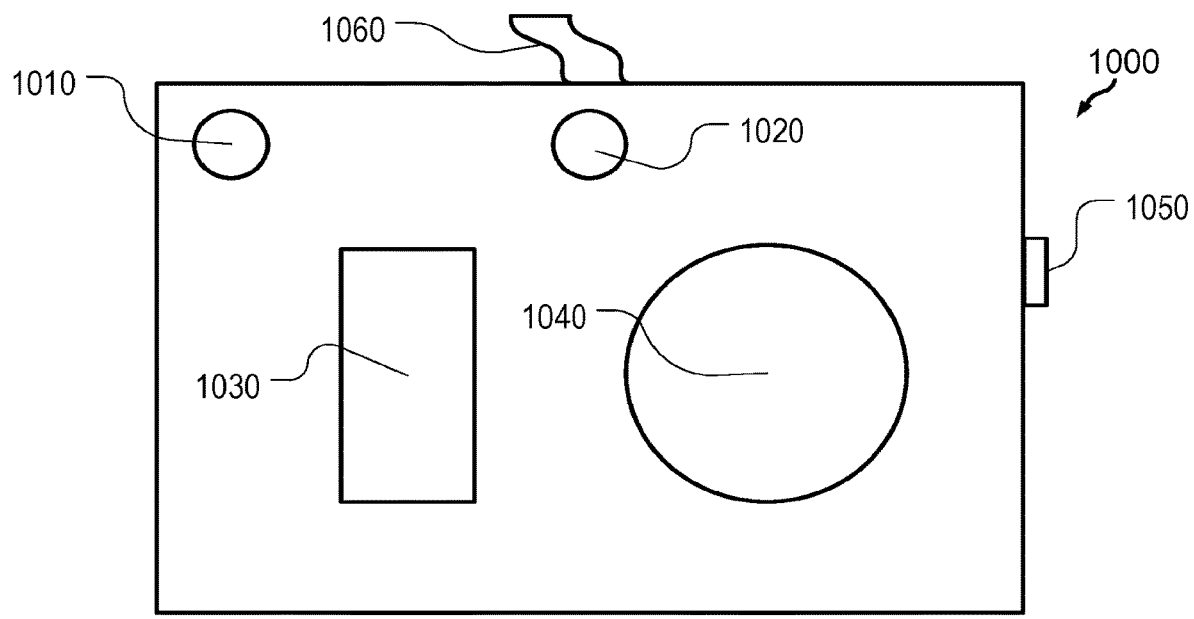
FIG. 10 is a simplified diagram of another input control console using touch-sensitive input controls according to some embodiments.

FIG. 10 is a simplified diagram of an input control console 1000 using touch-sensitive input controls according to some embodiments. Similar to input control console 400, input control console 1000 includes an emergency stop button 1010 similar to emergency stop button 410 and a display selection button 1020 similar to display selection switch 420.

Input control console 1000, further includes a first touch-sensitive input control 1030 providing at least one axis of touch sensitivity. And although FIG. 10 shows first touch-sensitive input 1030 as being rectangular in shape, other elongate shapes suitable for providing at least one axis of touch sensitivity are possible. In some examples, first touch-sensitive input control 1030 is usable to provide insertion and/or retraction movement commands by having the operator drag a finger and/or a stylus along first touch-sensitive input control 1030 in a first direction to indicate insertion and in an opposite direction to indicate retraction. And, although first touch-sensitive input control 1030 is positioned for operation by the left hand of the operator, first touch-sensitive input control 1030 could alternatively be located to the right side of input control console 1000 for operation by the right hand of the operator.

In some examples, contact with and/or dragging of the finger and/or stylus along first touch-sensitive input control 1030 may be detected by the one or more circuit boards, logic boards, and/or the like of input control console 1000 using combinations of one or more emitters, electrodes, conductors, and/or the like. In some examples, first touch-sensitive input control 1030 may operate using any touch-sensitive technique including resistive, capacitive, infrared, ultrasonic, and/or the like. In some examples, a scale factor between a length of drag along first touch-sensitive input control 1030 and amount of insertion and/or retraction movement by the elongate device is adjustable by the operator and/or control software of the elongate device so that an insertion/retraction velocity of the elongate device relative to an angular velocity of the scroll wheel may be adjusted to allow both fast insertion and retraction when advantageous and slower more precise insertion and retraction when greater control precision is desired.

In some examples, first touch-sensitive input control 1030 may further be tap sensitive through the use of one or more switches located below first touch-sensitive input control 1030 or by the detection of a more forceful press on first touch-sensitive input control 1030. In some examples, the tap sensitivity may be used to implement a camera cleaning input control. In some examples, tapping of first touch-sensitive input control 1030 triggers the cleaning mechanisms of the endoscope, which may optionally affect the amount of air and/or other gasses blown across the one or more lenses based a duration, force, and/or location of the tap.

In some embodiments, first touch-sensitive input control 1030 may be flush mounted and/or slightly raised to support easy cleaning and/or sterilization of input control console 1000. In some embodiments, first touch-sensitive input control 1030 is optionally mounted within a raised ring or on a raised bezel (not shown). In some examples, the raised ring is similar to raised ring 436 and may be used to attach a surgical and/or sterile drape to input control console 1000, such as is described with respect to process 940.

Input control console 1000, further includes a second touch-sensitive input control 1040 providing two axes of touch sensitivity. And although FIG. 10 shows second touch-sensitive input 1040 as being circular in shape, other shapes suitable for providing two axes of touch sensitivity, such as a square or rectangle, are possible. In some examples, second touch-sensitive input control is usable to provide pitch and/or yaw steering commands by having the operator drag a finger and/or a stylus along second touch-sensitive input control 1040 in any direction across a surface of second touch-sensitive input control 1040. In some examples, the vertical and/or horizontal components of direction of drag are then used to change a pitch and a yaw setting, respectively, for the distal end of the elongate device. In some examples, location of a position of the finger or stylus relative to a center of second touch-sensitive input control 1040 may be used to determine the pitch and/or the yaw setting for the distal end of the elongate device. In some examples, the pitch and/or yaw settings are usable to control the distances each of the cables extending between the proximal and distal ends of the elongate device are pushed and/or pulled. And, although second touch-sensitive input control 1040 is positioned for operation by the right hand of the operator, second touch-sensitive input control 1040 could alternatively be located to the left side of input control console 1000 for operation by the left hand of the operator.

In some examples, contact with and/or dragging of the finger and/or stylus along second touch-sensitive input control 1040 may be detected by the one or more circuit boards, logic boards, and/or the like of input control console 1000 using combinations of one or more emitters, electrodes, conductors, and/or the like. In some examples, second touch-sensitive input control 1040 may operate using any touch-sensitive technique including resistive, capacitive, infrared, ultrasonic, and/or the like. In some examples, a scale factor between a length of drag along second touch-sensitive input control 1040 and an amount of pitch and/or yaw imparted to the distal end of the elongate device is adjustable by the operator and/or control software of the elongate device.

In some examples, second touch-sensitive input control 1040 may further be tap sensitive through the use of one or more switches located below second touch-sensitive input control 1040 or by the detection of a more forceful press on first touch-sensitive input control 1030. In some examples, the tap sensitivity may be used to cycle through operational modes supported by the elongate device, with each detected tap of second touch-sensitive input control 1040 resulting in switching to a next operational mode in the cycle. In some examples, different regions of second touch-sensitive input control 1040 may be independently tap sensitive allowing taps in different regions of second touch-sensitive input control 1040 to result in switching to a corresponding operational mode. In some examples, the operational modes may correspond to the locked and controlled modes as previously discussed with respect to input control console 400. In some examples, the current operational mode may optionally be indicated using one or more indicators, such as LEDs, illuminated icons, a display (e.g., a liquid crystal display), and/or the like.

In some embodiments, second touch-sensitive input control 1040 may be flush mounted and/or slightly raised to support easy cleaning and/or sterilization of input control console 1000. In some embodiments, second touch-sensitive input control 1040 is optionally mounted within a raised ring or on a raised bezel (not shown). In some examples, the raised ring is similar to raised ring 448 and may be used to attach the surgical and/or sterile drape to input control console 1000, such as is described with respect to process 940.

Similar to input control console 400, input control console 1000 further includes a passive control button 1050 similar to passive control button 450. Although passive control button 1050 is shown mounted on a side of input control console 1000, location of passive control button 1050 may optionally be elsewhere, such as by being integrated with the operational mode selection using taps of second touch-sensitive input control 1040.

Also similar to input control console 400, input control console 1000 further includes one or more cables 1060 similar to the one or more cables 470, one or more self-contained power sources (not shown), one or more coils for receiving power inductively (not shown), and/or a mounting flange (not shown) similar to mounting flange 490.

As discussed above and further emphasized here, FIG. 10 is merely an example which should not unduly limit the scope of the claims. One of ordinary skill in the art would recognize many variations, alternatives, and modifications. In some embodiments, input control console 1000 may optionally further include a raised wrist rest usable to provide a resting point for the wrists of the operator and/or to provide good ergonomic positioning of the operator's hands over the other input controls. In some examples, the wrist rest is optionally padded. In some examples, a height of the wrist rest relative to the rest of input control console 1000 is adjustable.

In some embodiments, first touch-sensitive input control 1030 and second touch-sensitive input control 1040 may be replaced by a combined touch-sensitive input control having different drag and/or tap regions to support each of the input controls for input control console 1000 as discussed above.

In some embodiments, the combined touch-sensitive input control may optionally be implemented using a touch-sensitive screen. In some examples, the display features of the touch-sensitive screen may be used to display a user interface having regions corresponding to the various buttons, selectors, touch-sensitive input controls, and/or the like described for both input control consoles 400 and/or 1000. In some examples, the user interface may be configurable to change a size, shape, orientation, color, and/or location of the of input controls allowing, for example, easy changes between which sides the insertion/retraction and steering input controls are located. In some examples, the user interface may support access to menus to configure the scale factors and/or other characteristics of the input controls. In some examples, the user interface may also include a region that is part of display system 110 and, for example, may be usable to display the endoscopic views, the model of the anatomy, the targeting indicators, the alignment indicators, and/or the like.

ADDITIONAL EXAMPLES

A1. An example method of draping an input control console of an elongate device with a surgical drape comprises: positioning a main drape section of the surgical drape over an input control console using a first opening at one end of the main drape section; aligning each of a plurality of pockets in the surgical drape over a respective raised ring or bezel on the input control console, each of the plurality of pockets is sized to enable user interaction with an underlying infinite length of travel control input located within a boundary of the respective raised ring or bezel to which it is anchored; anchoring a second opening in each of the plurality of pockets to the respective raised ring or bezel using a tightening element; and closing the first opening of the surgical drape using a closure element attached to the main drape section near the first opening.

A2. The method of example A1, further comprising operating the infinite length of travel input control on the input control console by moving excess material of each of the plurality of pockets over the infinite length of travel input control.

A3. The method of example A1 or A2, further comprising expelling air from each of the plurality of pockets before anchoring each of the plurality of pockets to the respective raised ring or bezel.

A4. The method of any of examples A1-A3, further comprising expelling air from the surgical drape before closing the first opening.

A5. The method of any of examples A1-A4, wherein each of the plurality of pockets comprises excess drape material which is movable relative to the respective raised ring or bezel to which it is anchored.

A6. The method of any of examples A1-A5, wherein each of the plurality of pockets is stretchable at the pocket opening between an expanded size and a collapsed size and wherein the collapsed size is smaller than a circumference of the respective raised ring or bezel to which the pocket is anchored.

A7. The method of any of examples A1-A6, wherein a first material of the main drape section is different from a second material of each of the plurality of pockets.

A8. The method of any of examples A1-A7, wherein a material of the main drape section is a clear polyethylene with a thickness between 1.5 and 2.0 mils.

A9. The method of any of examples A1-A7, wherein a material of each of the plurality of pockets is a clear low-density polyethylene with a thickness between 1.0 and 1.5 mils.

One or more elements in embodiments of the invention (e.g., the processing of signals received from the input controls and/or control of the elongate device) may be implemented in software to execute on a processor of a computer system, such as control system 112. When implemented in software, the elements of the embodiments of the invention are essentially the code segments to perform the necessary tasks. The program or code segments can be stored in a non-transitory machine-readable storage media, including any media that can store information including an optical medium, semiconductor medium, and magnetic medium. Machine-readable storage media examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. As described herein, operations of accessing, detecting, initiating, registered, displaying, receiving, generating, determining, moving data points, segmenting, matching, etc. may be performed at least in part by the control system 112 or the processors thereof.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A drape for an input control console of an elongate device, the drape comprising:

a main drape section configured to fit over the input control console via a main opening at one end of the main drape section; and a plurality of pockets;

wherein:

each of the plurality of pockets includes a pocket opening that is attached to a respective secondary opening in the main drape section; and each of the plurality of pockets is configured to be anchored, at the pocket opening, to a side surface of a respective raised ring or bezel on the input control console using a respective tightening element.

2. The drape of claim 1, wherein each of the plurality of pockets is sized to enable user interaction with an underlying infinite length of travel control input located within a boundary of the respective raised ring or bezel.

3. The drape of claim 1, wherein each of the plurality of pockets comprises excess drape material which is movable relative to the respective raised ring or bezel to which it is anchored.

4. The drape of claim 1, wherein each of the plurality of pockets is stretchable at its pocket opening between an expanded size and a collapsed size and wherein the collapsed size is smaller than a circumference of the respective raised ring or bezel to which the pocket is anchored.

5. The drape of claim 1, wherein a first material of the main drape section is different from a second material of each of the plurality of pockets.

6. The drape of claim 1, wherein the main drape section is a different thickness than each of the plurality of pockets.

7. The drape of claim 1, wherein a material of the main drape section is a clear polyethylene with a thickness between 1.5 and 2.0 mils.

8. The drape of claim 1, wherein a material of each of the plurality of pockets is a clear low-density polyethylene with a thickness between 1.0 and 1.5 mils.

9. The drape of claim 1, further comprising a closure element located at an end of the main drape section near the main opening, the closure element being configured to secure the drape at the main opening around one or more cables or a mounting mechanism of the input control console.

10. The drape of claim 1, wherein the main drape section is tubular in shape.

11. The drape of claim 1, further comprising a cuff located at the main opening.

12. The drape of claim 1, wherein each respective secondary opening corresponds to a respective slit in the main drape section.

13. The drape of claim 1, wherein each respective pocket opening is attached around the respective secondary opening by heat fusion or a double-sided adhesive tape.

14. The drape of claim 1, wherein each respective tightening element is selected from a group consisting of an elastic band, a draw string, and a tape strip.

15. The drape of claim 14, wherein each respective tightening element is integrated into the drape.

16. A method of making a drape with an input control console of an elongate device, the method comprising:

forming a plurality of pockets by folding respective first pieces of drape material in half and fusing together first sides of each respective first piece of drape material;

attaching each of the plurality of pockets to a respective slit in a second piece of draping material by fusing respective second sides of a first opening in each of the plurality of pockets to third sides of the respective slit;

folding the second piece of draping material and fusing together outer edges of the second piece of draping material to form a tube;

fusing closed a first end of the tube; and attaching a closure element to a second opening in the drape located at a second end of the tube opposite to the first end.

17. The method of claim 16, further comprising:

inserting a respective spacer through each first opening in each of the plurality of pockets before attaching each of the plurality of pockets to the respective slit; and removing the respective spacer after attaching each of the plurality of pockets to the respective slit.

18. The method of claim 16, wherein the first sides of each respective first piece of drape material are fused interior to the first sides to create a desired shape for each of the plurality of pockets.

19. A method of using a drape with an input control console of an elongate device, the method comprising:

slipping a main drape section of the drape over an input control console using a first opening at one end of the main drape section;

aligning each of a plurality of pockets in the drape over a respective raised ring or bezel on the input control console;

anchoring a second opening in each of the plurality of pockets to the respective raised ring or bezel using a tightening element; and closing the first opening of the drape using a closure element attached to the main drape section near the first opening.

20. The method of claim 19, further comprising operating an infinite length of travel input control on the input control console by moving excess material of one of the plurality of pockets over the infinite length of travel input control.

* * * * *